US009023827B2

(12) United States Patent
Paufique

(10) Patent No.: US 9,023,827 B2
(45) Date of Patent: May 5, 2015

(54) ACTIVE INGREDIENT WITH CUTANEOUS APPLICATION OBTAINED FROM METSCHNIKOWIA AGAVES AND USES FOR IMPROVING THE STATE OF THE SKIN

(71) Applicant: Societe Industrielle Limousine d'Application Biologique, Objat (FR)

(72) Inventor: Jean Paufique, Objat (FR)

(73) Assignee: Societe Industrielle Limousine d'Application Biologique, Objat (FR)

( * ) Notice: Subject to any disclaimer, the term of this patent is extended or adjusted under 35 U.S.C. 154(b) by 44 days.

(21) Appl. No.: 13/859,771

(22) Filed: Apr. 10, 2013

(65) Prior Publication Data
US 2013/0274221 A1 Oct. 17, 2013

(30) Foreign Application Priority Data

Apr. 16, 2012 (FR) ...................... 12 53471

(51) Int. Cl.
*A01N 43/04* (2006.01)
*A61K 31/715* (2006.01)
*A61K 8/60* (2006.01)
*A61Q 19/08* (2006.01)
*C07H 3/06* (2006.01)
*A61K 8/99* (2006.01)
*A61K 8/73* (2006.01)

(52) U.S. Cl.
CPC . *A61K 8/60* (2013.01); *A61Q 19/08* (2013.01); *C07H 3/06* (2013.01); *A61K 8/99* (2013.01); *A61K 8/736* (2013.01)

(58) Field of Classification Search
None
See application file for complete search history.

(56) References Cited

U.S. PATENT DOCUMENTS

| 6,531,132 B1 | 3/2003 | Paufique |
| 6,875,754 B1 * | 4/2005 | Griesbach et al. ............. 514/54 |
| 2012/0164121 A1 | 6/2012 | Paufique |

FOREIGN PATENT DOCUMENTS

| FR | 2 797 186 | 2/2001 |
| FR | 2 949 684 | 3/2011 |
| JP | 2002-370960 | 12/2002 |
| JP | 2005-15348 | 1/2005 |
| WO | 03/068243 | 8/2003 |

OTHER PUBLICATIONS

Escalante et al. International Journal of Food Microbiology (2008), vol. 124, pp. 126-134.*
French Search Report dated Jan. 9, 2013, corresponding to the Foreign Priority Appln. No. 12 53471.

* cited by examiner

*Primary Examiner* — Patrick Lewis
(74) *Attorney, Agent, or Firm* — Young & Thompson

(57) ABSTRACT

An active ingredient with cutaneous application obtained from *Metschnikowia agaves*, as well as its use for preventing and/or combating ageing of the skin and its visible manifestations, and cosmetic compositions including this active ingredient and to a cosmetic process for skin care.

17 Claims, No Drawings

ACTIVE INGREDIENT WITH CUTANEOUS APPLICATION OBTAINED FROM METSCHNIKOWIA AGAVES AND USES FOR IMPROVING THE STATE OF THE SKIN

FIELD OF THE INVENTION

This invention relates to an active ingredient obtained from *Metschnikowia agaves*, as well as its use for improving the state of the skin, in particular for combating cutaneous ageing and improving the perceived age.

The invention also relates to the cosmetic compositions including this active ingredient, and a process of cosmetic treatment that is intended to prevent and/or to combat cutaneous ageing.

BACKGROUND OF THE INVENTION

The skin is a complex organ that covers the entire surface of the body and performs numerous vital functions. It is constantly subjected to attacks, both external and internal, which can threaten its balance and its appearance.

This is why active ingredients are sought that are capable of protecting the skin against these attacks that can alter its proper operation and its appearance and of combating the manifestations that are derived therefrom.

In particular, within the cosmetic field, active ingredients are sought for the treatment of skin essentially so as to act on the biomechanical properties of the skin and to use anti-ageing, hydrating and anti-wrinkle characteristics.

SUMMARY OF THE INVENTION

To respond to this problem, the purpose of this invention is an active ingredient that is obtained from *Metschnikowia agaves* and its use within a composition with cutaneous application that is intended for the treatment of the skin.

*Metschnikowia agaves* Lachance is a yeast belonging to the class of Saccharomycetes and to the Metschnikowiaceae family. Having a long-oval shape, it appears in the form of white colonies. Its method of reproduction is vegetative by budding.

*Metschnikowia agaves*, thus designated according to the name of its host, was isolated from the blue agave of Mexico, used for the production of tequila.

The use of this yeast in the cosmetic and/or dermopharmaceutical field has never been considered.

However, in a surprising way, *Metschnikowia agaves* has remarkable properties at the level of the skin and integuments.

Advantageously, the use of *Metschnikowia agaves* makes it possible to improve the state of the skin, in particular to prevent and/or to combat the effects of cutaneous ageing. According to a particular advantage, the use of *Metschnikowia agaves* on the skin makes it possible in particular to act in a specific way on hyaluronic acid, with one of the markers that is essential and recognized for its importance in anti-ageing care currently existing. However, other yeasts do not allow such effectiveness.

The objects of the invention are also the cosmetic compositions for topical application comprising an active ingredient that is obtained from *Metschnikowia agaves*, as well as a cosmetic process for care of human skin, intended to prevent and/or to combat the effects of age on the skin, comprising the topical application of a composition containing an active ingredient that is obtained from *Metschnikowia agaves*.

This invention is now described in detail.

DETAILED DESCRIPTION OF THE INVENTION

Use

According to a first aspect, the object of the invention is an active ingredient that is obtained from *Metschnikowia agaves* for its use as active ingredient in a composition with cutaneous application, with said active ingredient and/or said composition being intended to improve the state of the skin, in particular to prevent and/or to combat the effects of cutaneous ageing.

The active ingredients obtained from yeasts can be of two types. These are either:
- molecules produced from yeasts; these are only molecules produced by the yeasts and not the yeasts themselves that are used; or
- active ingredients obtained from yeasts themselves.

These two types of active ingredients are different. In the first case, the molecules produced by one yeast can possibly be produced by other types of yeasts, whereas in the second case, the active principle is completely dependent on the choice of the yeast.

An "active ingredient obtained from *Metschnikowia agaves*", within the meaning of the present invention, means an active ingredient obtained from the yeast *Metschnikowia agaves* itself and not a molecule or a mixture of molecules produced by the yeast *Metschnikowia agaves*.

A "composition for cutaneous application", within the meaning of the present invention, means any composition intended to be applied onto the skin, preferably a cosmetic composition.

In terms of the invention, "composition with cutaneous application" is defined as any composition intended to be applied on the skin, preferably a cosmetic composition.

Advantageously, an active ingredient that is obtained from *Metschnikowia agaves* actually makes it possible to improve the state of the skin, in particular to prevent and/or to combat the effects of cutaneous ageing, specifically to hydrate the skin, to smooth the facial features, and to reduce wrinkles.

According to the invention, an active ingredient that is obtained from *Metschnikowia agaves* is capable in particular of ensuring high-performing effectiveness on one of the essential markers for ageing of the skin, hyaluronic acid.

Hyaluronic acid is the most abundant component of the skin and structure with collagen and elastin, the support tissue of the dermis. Owing to its strong hydroscopy, it has a unique ability to collect and bond a large amount of water and to fill, in the form of a hydrated gel, the gaps between fibrillar components of the extracellular matrix. It thus ensures the hydration of the skin as well as the maintenance of its flexibility and its plasticity.

Hyaluronic acid is a non-sulfated glycosaminoglycan that consists of repeated disaccharide units of N-acetylglycosamine and glucuronic acid. Its synthesis is ensured by the hyaluronan synthases (HAS1, HAS2, and HAS3) and its degradation by the hyaluronidases.

During cutaneous ageing, the dermal contents of hyaluronic acid are reduced; its enzymes from synthesis also decrease whereas the level of its enzymes from degradation increases. These changes are reflected by a reduction of the water content of the skin and the loss of its elasticity and the appearance of wrinkles.

According to the invention, an active ingredient that is obtained from *Metschnikowia agaves* makes it possible to stimulate the natural synthesis of:
- The enzyme HAS2 from synthesis, and
- Hyaluronic acid.

An active ingredient that is obtained from *Metschnikowia agaves* applied on the skin therefore makes it possible to reactivate the natural mechanism for synthesis of the hyaluronic acid for consolidating the dermal blanket, hydrating the skin, and smoothing out wrinkles.

Advantageously, it has a targeted action in depth that makes it possible to improve the state of the skin: the skin is more hydrated, the facial features are visibly smoothed, and wrinkles are reduced, in particular at the level of crow's feet.

According to one particularly suitable embodiment, the purpose of the invention is the use in a composition of an active ingredient that is obtained from *Metschnikowia agaves*, as described below.

Active Ingredient

The invention relates to an active ingredient that is intended for use in a composition with cutaneous application, obtained from *Metschnikowia agaves*.

According to a particular embodiment, it involves a *Metschnikowia agaves* hydrolyzate. "Hydrolyzate" is defined as any extract that is obtained from *Metschnikowia agaves*, comprising at least one hydrolysis stage of *Metschnikowia agaves*.

Preferably, the active ingredient according to the invention comprises oligosaccharides; even more preferably, the active ingredient according to the invention comprises oligosaccharides with a degree of polymerization of between 2 and 17, compounds in particular of α-glucan oligosaccharides and β-glucan oligosaccharides.

The active ingredient preferably has a clear yellow color.

It can come in clear liquid form and can be defined by at least one, preferably all, of the characteristics disclosed below.

Dry Materials

The level of dry materials of an active ingredient according to the invention (measured by running a sample with a given initial weight through the oven at 105° C. in the presence of sand until a constant weight is obtained) can be between 20 and 100 g/l, preferably between 35 and 50 g/l.

Measurement of the pH

The pH (measured by the potentiometric method at ambient temperature) can be between 4 and 5, preferably between 3.5 and 5.5.

Carbohydrates

Determination of the Total Sugar Content

The metering of the total sugar content can be implemented by the DUBOIS method (DUBOIS, M. et al., (1956), Analytical Chemistry, 28, No. 3, pp. 350-356). In the presence of concentrated sulfuric acid and phenol, the reducing sugars provide an orangey-yellow compound. From a standard range, it is possible to determine the total sugar level of a sample.

Preferably, the total sugar content is between 9 and 48 g/l, in particular between 16 and 24 g/l.

The total sugar content is therefore greater than 9% by weight of dry material. In particular, it can be between 32 and 69% by weight of dry material.

Characterization of the Carbohydrate Fraction:

The determination of the size of the carbohydrates of an active ingredient according to the invention is made by high-performance liquid chromatography.

The chromatogram that is obtained shows the presence of monosaccharides of a molecular weight that is less than 180 Da and oligosaccharides and polysaccharides with a molar mass of between 180 and 18,500 Da (degree of polymerization at most 103). The monosaccharides represent less than 37%, preferably between 25 and 37%, and the oligosaccharides and polysaccharides of molar mass of between 180 and 18,500 Da represent at least 63%, in particular between 63 and 75% of oligosaccharides with a degree of polymerization of between 2 and 42, preferably between 2 and 17.

The simple sugars of the active ingredient according to the invention preferably consist of glucose and mannose.

So as to better characterize the sugars of the active ingredient according to the invention, enzymatic hydrolyses were implemented with an α-amylase and a β-glucanase. These hydrolyses make it possible to demonstrate whether the glucose is present in the form of α-glucans and β-glucans.

The analyses show that the bonded glucose is present in the form of α-glucan oligosaccharides and in the form of β-glucan oligosaccharides.

The glucidic fraction of this invention consists of monosaccharides and oligosaccharides with a degree of polymerization that for the most part is between 2 and 17. The active ingredient contains glucose and mannose. The oligosaccharides consist in particular of α-glucans and β-glucans.

It is in particular this fraction that imparts to the active ingredient according to the invention an effect on the improvement of the state of the skin, in particular for combating cutaneous ageing.

Production Process

The active ingredient according to the invention as described above can preferably be obtained by a process that comprises hydrolysis.

A particularly suitable process comprises at least the series of the following stages:
Solubilization of *Metschnikowia agaves* yeasts in an aqueous solution, and
Hydrolysis.

Preferably, the hydrolysis is enzymatic hydrolysis.

According to a particularly suitable embodiment, the process comprises at least the series of the following stages:
Solubilization of *Metschnikowia agaves* yeasts in an aqueous solution,
Enzymatic hydrolysis,
Enzymatic inactivation by heat treatment,
Filtration,
Purification,
Filtration and sterilizing filtration.

Stages of deodorization and discoloring or concentration can be added.

The parameters of the different stages should be adjusted so as to obtain active ingredients comprising oligosaccharides, preferably oligosaccharides with a degree of polymerization that is primarily between 2 and 17.

Cosmetic Compositions and Cosmetic Skin Care Process

This invention also covers the cosmetic compositions that include an active ingredient that is obtained from *Metschnikowia agaves*, in different galenical forms, adapted to administration by cutaneous topical means.

These compositions can come in particular in the form of oil-in-water emulsions, water-in-oil emulsions, multiple emulsions (water/oil/water or oil/water/oil) that can optionally be microemulsions or nanoemulsions, or in the form of solutions, suspensions, hydrodispersions, aqueous gels or powders. They can be more or less fluid and have the appearance of a cream, a lotion, a milk, a serum, an ointment, a gel, a paste or a foam, or in solid form.

It may involve compositions comprising between 0.1 and 3% of active ingredient(s) obtained from *Metschnikowia agaves* according to this invention.

These compositions comprise, in addition to the active ingredient, a physiologically acceptable and preferably cosmetically acceptable medium, i.e., which does not cause unacceptable feeling of discomfort for the user such as redness, tingling, or stinging.

As an additive, the compositions according to the invention can contain at least one compound that is selected from among:
Oils, which can be selected in particular from among volatile or non-volatile, linear or cyclic, silicone oils;
Waxes, such as ozokerite, polyethylene wax, beeswax, or carnauba wax;
Silicone elastomers,
Surfactants, preferably emulsifying, whether they are non-ionic, anionic, cationic, or amphoteric;
Co-surfactants, such as linear fatty alcohols;
Thickeners and/or gelling agents, Moisturizers, such as polyols like glycerin;

Organic filters,

Inorganic filters,

Dyes, preservatives, feedstocks,

Tightening agents,

Sequestering agents,

Perfumes,

And their mixtures, without this list being limiting.

Examples of such additives are cited in particular in the Dictionnaire CTFA (International Cosmetic Ingredient Dictionary and Handbook published by the Personal Care Product Council).

Of course, one skilled in the art will make sure to select the possible active or non-active complementary compounds and their amounts in such a way that the advantageous properties of the mixture are not, or essentially not, altered by the addition being considered.

These compositions are intended in particular to promote improving the state of the skin, in particular to prevent and/or to combat the effects of age on the skin. For this purpose, the object of the invention is a cosmetic process for care of human skin, intended to prevent and/or to combat the effects of age on the skin, comprising the topical application of a composition that contains an active ingredient that is obtained from *Metschnikowia agaves* according to this invention.

EXAMPLES

A nonlimiting example of the process for producing an active ingredient obtained from *Metschnikowia agaves* is presented below, as well as examples of compositions including such an active ingredient.

Example 1

Process for the Production of the Active Ingredient According to the Invention

An example of a process for producing an active ingredient according to the invention comprises the implementation of the following stages:

Solubilization of *Metschnikowia agaves* yeasts in the water in a basic medium at a rate of 20 g/l.

Enzymatic hydrolysis of sugars,

Enzymatic inactivation by heat treatment,

Filtration and purification by recovery of the filtrate,

Concentration,

Filtration and sterilizing filtration.

The active ingredient that is obtained has the following characteristics:

Appearance: clear aqueous solution

Color: clear yellow

Content of dry materials: 40.5 g/l pH: 4.3

Total sugar content: 21.7 g/l, or 53.7% of sugars relative to the dry material, including 69% in the form of oligosaccharides with a degree of polymerization of between 2 and 17 in the form of glucose and mannose, Protein content: 23.5%

Ash content: 22.8%.

Example 2

Use of an Active Ingredient According to the Invention in a Daily Cream

| Phase A. | Water | Enough to make 100% |
|---|---|---|
| | Glycerin | 1% |
| Phase B. | DUB GMS AE (Stéarinerie DUBOIS) | 1.3% |
| | DUB SEG (Stéarinerie DUBOIS) | 1% |
| | Cetearyl alcohol | 1.3% |
| | DUB MCT 5545 (Stéarinerie DUBOIS) | 6.2% |
| | Lanol 99 (Seppic) | 4% |
| | Cetyl palmitate | 0.8% |
| | Sophiderm MC30 (Sophim) | 3.4% |
| | Palm oil (Sictia) | 1% |
| Phase C. | Active ingredient according to the invention (Example 1) | 3% |
| | Preservative | 0.7% |

The amounts that are indicated are provided in percentage by weight.

This white, meltingly soft, creamy emulsion has a pH of 5.5. In topical application on the skin, it has a rapid penetration with a soft finish.

It can be obtained by implementing the following stages:

Mixing A, heating in a water bath at 80° C. while being stirred magnetically,

Mixing B, heating in a water bath at 80° C. while being stirred magnetically,

Emulsifying B in A with a rotor-stator at 1,600 rpm,

At 30° C., adding C, in the order indicated, with a rotor-stator at 1,500 rpm, and Leaving it to cool with a rotor-stator until homogenization of the emulsion is completed.

Example 3

Use of an Active Ingredient According to the Invention in a Night Cream

| Phase A. | Water | Enough to make 100% |
|---|---|---|
| Phase B. | DUB LAHE (Stéarinerie DUBOIS) | 5% |
| | DUB ZENOATE (Stéarinerie DUBOIS) | 5% |
| | Montanov 202 (Seppic) | 4% |
| | Montanov 14 (Seppic) | 4% |
| | Montanov S (Seppic) | 1% |
| | DUB 340 (Stéarinerie DUBOIS) | 3% |
| | DUB Lilirose (Stéarinerie DUBOIS) | 6% |
| | DUB PIS (Stéarinerie DUBOIS) | 6% |
| | DUB PPH1 (Stéarinerie DUBOIS) | 4% |
| Phase C. | Preservative | 0.7% |
| | Active ingredient according to the invention (Example 1) | 3% |

The amounts that are indicated are provided in percentage by weight.

This white compact emulsion has a pH of 5.5. In topical application, it has a light application, with a dry finish and a film-forming effect.

It can be obtained by the implementation of the following stages:

Heating A in a water bath at 80° C. while being stirred magnetically,

Mixing B, heating in a water bath at 80° C. while being stirred magnetically,

Emulsifying B in A with a rotor-stator at 3,200 rpm,

At 40° C., adding C, in the order indicated, with a rotor-stator at 3,000 rpm,
Leaving it to cool while being stirred.

Example 4

Use of an Active Ingredient According to the Invention in a Plumping Serum

| Phase A. | Water | Enough to make 100% |
|---|---|---|
| | Viscolam AT64P (Rita) | 3.4% |
| | Glycerin | 6% |
| | Sterol CC5595 (Alpinia) | 3.4% |
| | Simulsol 1292 (Seppic) | 3.4% |
| | Phonoemuls 100 (Phoenix Chemical) | 2.7% |
| | Preservative | 0.7% |
| | Active ingredient according to the invention (Example 1) | 3% |

The amounts that are indicated are provided in percentage by weight.

This transparent, creamy gel has a pH of 7. It spreads easily, and it has a quick penetration with a dry and soft finish.

It can be obtained by the implementation of the following stages:
Mixing A, in order while being stirred mechanically at 2,000 rpm,
Leaving it to stir mechanically until cooling is completed.

Example 5

Use of an Active Ingredient According to the Invention in a Covering Foam

| Phase A. | Water | Enough to make 100% |
|---|---|---|
| | Carbopol ETD2050 (Noveon) | 0.7% |
| Phase B. | AAB2 (Aiglon) | 2% |
| | Micronized stearin TP (Stéarinerie Dubois) | 2% |
| | DUB GMS AE (Stéarinerie Dubois) | 2% |
| | DUB RG AE (Stéarinerie Dubois) | 2.7% |
| | DUB IPM (Stéarinerie Dubois) | 3% |
| Phase C. | Preservative | 0.7% |
| | Active ingredient according to the invention (Example 1) | 3% |
| Phase D. | Titanium dioxide | 3.4% |
| | Kaolin | 2% |

The amounts that are indicated are provided in percentage by weight.

This white, foamy, emulsified gel has a pH of 5.8. With topical application, it has a comfortable spreading with a lightly film-forming cottony finish.

It can be obtained by the implementation of the following stages:
Mixing A, heating in a water bath at 80° C., while being stirred mechanically in ensuring that the gel is well-dispersed (approximately 800 rpm),
Mixing B, heating in a water bath at 80° C. while being stirred magnetically,
Emulsifying B in A with a rotor-stator at 2,200 rpm,
Adding C immediately in the order indicated with the rotor-stator at 2,200 rpm,
Leaving it to cool while being stirred,
Mixing the powdered phase D using a mortar,
At 30° C., adding D, little by little and while being stirred mechanically at 2,000 rpm, while ensuring its complete dispersion,
Leaving the foam that is produced to stir mechanically until its homogenization is completed.

Example 6

Use of an Active Ingredient According to the Invention in a Regenerating Fluid

| Phase A. | Water | Enough to make 100% |
|---|---|---|
| | Glycerin | 4% |
| | Blanose 7M31CF (Hercules) | 0.8% |
| Phase B. | DUB RG AE (Stéarinerie DUBOIS) | 3% |
| | DUB PPH1 (Stéarinerie DUBOIS) | 6.7% |
| | DUB MDIS (Stéarinerie DUBOIS) | 6.7% |
| | DUB MCT5545 (Stéarinerie DUBOIS) | 5.4% |
| Phase C. | Preservative | 0.7% |
| | Active ingredient according to the invention (Example 1) | 3% |

The amounts that are indicated are provided in percentage by weight.

This white, fluid, emulsified gel has a pH of 7.5. It has a comfortable spreading, a soft finish, and a hydrated effect.

It can be obtained by the implementation of the following stages:
Mixing A, heating in a water bath at 80° C., while being stirred mechanically in ensuring that the gel is well-dispersed (approximately 1,000 rpm),
Mixing B, heating in a water bath at 80° C. while being stirred magnetically,
Emulsifying B in A with a rotor-stator at 2,500 rpm,
At 30° C., adding C in order always with a rotor-stator at 2,200 rpm,
Leaving it to cool while being stirred until homogenization is completed.

Example 7

Use of an Active Ingredient According to the Invention in an Anti-Wrinkle Emulsion

| Phase A. | Water | Enough to make 100% |
|---|---|---|
| Phase B. | Montanov 68 (Seppic) | 2% |
| | Montanov 202 (Seppic) | 3% |
| | Lanol 99 (Seppic) | 5% |
| | Preservative | 0.7% |
| Phase C. | Active ingredient according to the invention (Example 1) | 3% |
| Phase D. | Sepigel 305 (Seppic) | 0.3% |

The amounts that are indicated are provided in percentage by weight.

This emulsion has a pH of 6.8.

It can be obtained by the implementation of the following stages:
Heating A in a water bath at 80° C.,
Mixing B in a pot and heating in a water bath at 80° C.,
Emulsifying A in B with a rotor-stator between 2,000 and 5,000 rpm,
At 50° C., adding C, and then D, still with a rotor-stator,
Leaving it to stir until cooling is completed.

Evaluation of the Cosmetic Effectiveness of an Active Ingredient According to the Invention A. In-Vitro Tests Study of the Effect on the Synthesis of Hyaluronic Acid The object of this study is to evaluate the effect of the active ingredient of Example 1 on the ability to increase the synthesis of hyaluronic acid.

The study was done on normal human fibroblasts by ELISA metering, according to the following operating procedure.

On D0, the human fibroblasts are inoculated in the complete medium. The cells are then incubated at 37° C. in an atmosphere containing 5% $CO_2$.

On D2, the culture medium is eliminated and replaced by the medium that contains the active ingredient of Example 1 at 0.5%, 1% and 2% (V/V). The TGF-β at 10 ng/ml is used as a positive control.

The cells are then incubated at 37° C. for 48 hours.

The supernatants are then recovered and stored at −80° C. on standby for ELISA metering.

The results of the metering are presented in the following table:

TABLE 1

|  | Synthesis of Hyaluronic Acid (ng/μg of Proteins) | Hyaluronic Acid Level/Control (%) |
| --- | --- | --- |
| Control | 1,280 |  |
| TGF-β, 10 ng/ml | 2,343 | +83 |
| Example 1 0.5% Active Ingredient | 1,878 | +47 |
| Example 1 1% Active Ingredient | 2,523 | +97 |
| Example 1 2% Active Ingredient | 4,309 | +237 |

These results clearly show that an active ingredient that is obtained from *Metschnikowia agaves* makes it possible to stimulate the synthesis of hyaluronic acid in the dermal cells.

In particular, tested at 2% on human fibroblasts, the active ingredient of Example 1 makes it possible to stimulate the synthesis of hyaluronic acid by 237%.

So as to demonstrate that this effectiveness is original and attached to the yeast that is the particular object of the invention, the same test was done on other 1% yeasts.

The results that are obtained are presented in Table 2 below:

TABLE 2

|  | Hyaluronic Acid Level/Control (%) |
| --- | --- |
| Example 1 1% Active Ingredient | +97% |
| Active Ingredient Obtained from 1% *Saccharomyces cerevisiae* | +24% |
| Active Ingredient Obtained from 1% *Candida saitoana* | +15% |

These results clearly show that all of the active ingredients that are obtained from yeasts do not have identical effectiveness and that the yeast that is the object of this invention is very different from yeasts used in cosmetic like *Saccharomyces cereviviae* and *Candida saitoana*.

Study of the Effect on the Expression of Hyaluronan Synthase-2

The objective of this study is to evaluate the effect of an ingredient on its ability to increase the expression of RNAm coding for hyaluronan synthase-2 (HAS2), an enzyme from the synthesis of hyaluronic acid.

The study was done by quantitative PCR on normal human fibroblasts according to the operating procedure described below.

On D0, the normal human fibroblasts are inoculated in the complete medium, and the cells are then incubated at 37° C.

On D1, the culture medium is eliminated and replaced by the SVF medium containing the active ingredient of Example 1 at 0.5%-1% and 2% (V/V). The TGF-β at 10 ng/ml is used as a positive control.

The cells are then incubated at 37° C. for 24 hours, the cells are recovered, and the total RNA are extracted.

The RNA have been reverse-transcripts, and the complementary DNA that are obtained have been analyzed by the quantitative PCR technique. The RNAm of the ribosomal protein S27, an internal reference control, were also analyzed concurrently with the RNAm of HAS2.

The quantification of the incorporation of fluorescence (SYBR Green) was measured continuously using a thermal cycler. The analysis of Ct (relative quantification) is done using suitable software.

The results of the metering are presented in the table below:

TABLE 3

|  | Level of HAS2 RNAm (%) | Effectiveness/ Control (%) |
| --- | --- | --- |
| Control | 100 |  |
| TGF-β, 10 ng/ml | 318 | +218 |
| Example 1 0.5% Active Ingredient | 252 | +152 |
| Example 1 1% Active Ingredient | 460 | +360 |
| Example 1 2% Active Ingredient | 751 | +651 |

These results clearly show that an active ingredient that is obtained from *Metschnikowia agaves* makes it possible to increase the expression of the RNAm coding for hyaluronan synthase-2.

In particular, tested at 2% on human fibroblasts, the active ingredient of Example 1 makes it possible to increase the expression of the RNAm coding for the hyaluronan synthase-2 of 651%.

B. In-Vivo Tests

Study of the Hydrating Effect: Comparison to Hyaluronic Acid

The objective of this study is to evaluate in vivo the hydrating effect of an active ingredient according to the invention that is formulated at 3% (composition of Example 7, comprising 0.13% of active ingredient by weight of dry material) in emulsion vs. placebo on the face. The effect of hyaluronic acid, reference molecule (formulated in an identical composition at 0.13% by weight of dry material), was also tested under the same conditions.

The study was done on half the face. The products were used randomly on 30 volunteers distributed in the following way:

Study of the placebo, 20 volunteers, mean age 58 years,

Study of the active ingredient according to the invention, 20 volunteers, mean age 59 years Study of hyaluronic acid, 20 volunteers, mean age 59 years.

The measurements of the water content were made at the bottom of the face using a MoisureMeter-D® before and after 28 days of twice-daily applications.

The MoisureMeter-D® generates a high-frequency electromagnetic wave that is sent via a probe onto the skin. The reflected electromagnetic wave is recorded; a dielectric constant proportional to the water content of the tissue that is measured is thus obtained. The higher the value of this constant, the greater the water content of the tissue. The probe used for taking measurements is the probe S15 that primarily measures the water content of the dermis. The operating procedure of the study is described below. Between D14 and D0, the volunteers apply a placebo cream over their entire faces.

On D0, the volunteers come to the laboratory without having applied product on their faces that morning (neither cream, nor make-up), and measurements are made with MOISTUREMETER-D® of the water content in each zone, and the products are distributed.

Between D0 and D27, the products are applied twice daily.

On D28, the volunteers come to the laboratory without having applied product on their faces that morning (neither cream, nor make-up), and measurements are made with MOISTUREMETER-D® of the water content in each zone.

The mean of the results obtained on the water content with the active ingredient or hyaluronic acid in percentage of those obtained with the placebo are presented in Table 4 below.

TABLE 4

|  | Variation/Placebo (%) |
| --- | --- |
| Example 1 3% Active Ingredient | +6.5% |
| 0.13% Hyaluronic Acid | +5.9% |

These results show that under the conditions of this study, after 28 days of twice-daily applications and in comparison to the placebo, the active ingredient according to the invention that is formulated with 3% emulsion significantly improves the hydration of the skin by increasing the water content. In addition, it is noted that the active ingredient according to the invention has an effect that is comparable to the one obtained with a reference hyaluronic acid formulated at 0.13% and tested under the same conditions.

Study of Anti-Wrinkle Properties: Comparison to Hyaluronic Acid

The objective of this study is to evaluate in vivo the anti-wrinkle effect of an active ingredient according to the invention (Example 1) that is formulated at 3% (composition of Example 7, comprising 0.13% of active ingredient by weight of dry material) in emulsion vs. placebo on crow's feet by fringe projection.

The effect of hyaluronic acid, reference molecule (formulated in an identical composition at 0.13% by weight of dry material), was also tested under the same conditions.

The study was carried out on half the face. The products were used randomly on 30 volunteers distributed in the following way:

The study of the placebo, 20 volunteers, mean age 58 years
The study of the active ingredient according to the invention, 20 volunteers, mean age 59 years
The study of hyaluronic acid, 20 volunteers, mean age 59 years.

3D acquisitions by fringe projection onto crow's feet were made before and after 28 days of twice-daily treatment.

The acquisitions were made using a fringe-projection device dedicated to 3D measurement of cutaneous relief. This system comprises a measurement sensor combining a light-fringe projector and a high-resolution CCD camera connected to acquisition software. A system for repositioning the volunteer's head along the 3 axes of movement makes it possible to find the same measurement zone again at different times during the study. The effect of the product is measured over a region of interest of 15×15 mm that is cut out automatically on the original acquisition.

The most pertinent parameters that are adopted for this study are:
3D roughness parameters:
Sq: Quadratic means of surface roughness
Sa: Arithmetic means of surface roughness
A volume parameter:
Negative volume: Volume less than the surface of the skin A reduction of these different parameters is characteristic of an improvement of the relief of the surface studied and a reduction of wrinkles.

The operating procedure of the study is described below.

Between D14 and D0, the volunteers apply a placebo cream over their entire faces.

On D0, volunteers come to the laboratory without having applied product on their faces that morning (neither cream, nor make-up), and 3D acquisitions by fringe projection onto crow's feet are made, and the products are distributed.

Between D0 and D27, the products are applied twice daily.

On D28, the volunteers come to the laboratory without having applied product on their faces that morning (neither cream, nor make-up), and 3D acquisitions by fringe projection onto crow's feet are made.

The mean of the results that are obtained, with the active ingredient or the hyaluronic acid in percentage of those obtained with the placebo, are presented in Table 5 below.

TABLE 5

|  | Variation/Placebo (%) | |
| --- | --- | --- |
|  | Example 1 3% Active Ingredient | 0.13% Hyaluronic Acid |
| Parameter Sq | −6.3% | −5.9% |
| Parameter Sa | −7.1% | −6.3% |
| Negative Volume | −14.2% | −10.6% |

These results show that under the conditions of this study, after 28 days of twice-daily applications and in comparison to the placebo, the active ingredient according to the invention that is formulated with 3% emulsion:

Smoothes the cutaneous relief at the crow's feet, since it reduces the parameter Sq by 6.3% and the parameter Sa by 7.1%,
Reduces the wrinkles by making possible a reduction of their volume (−14.2%).

In addition, it is noted that the active ingredient according to the invention has an effect that is comparable to the one obtained with hyaluronic acid, reference molecule, formulated at 0.13% and tested under the same conditions, and for all of the parameters that are studied.

The invention claimed is:

1. An active ingredient intended for use in a composition with cutaneous application, obtained from *Metschnikowia agaves*, wherein said active ingredient is *Metschnikowia agaves* hydrolyzate.

2. The active ingredient according to claim 1, comprising carbohydrates.

3. The active ingredient according to claim 1, comprising oligosaccharides.

4. The active ingredient according claim 3, wherein the oligosaccharides have a degree of polymerization of between 2 and 42.

5. The active ingredient according to claim 3, wherein the oligosaccharides are α-glucan oligosaccharides and β-glucan oligosaccharides and have a degree of polymerization of between 2 and 17.

6. The active ingredient according to claim 3, wherein the oligosaccharides are at least 63% by weight of total sugars present in the active ingredient.

7. The active ingredient according to claim 1, wherein the active ingredient is in a liquid form, and the active ingredient has:
- a level of dry materials of between 35 and 50 g/l, and
- a total sugar level of between 16 and 24 g/l.

8. A method for improving the state of the skin comprising:
cutaneously applying to the skin of a subject in need thereof, an effective amount of a cosmetic composition comprising said active ingredient according to claim 1, wherein said active ingredient and/or said composition improve the state of skin.

9. The method according to claim 8, wherein said active ingredient and/or said composition improves the state of skin by combating the ageing of the skin.

10. The method according to claim 8, wherein said active ingredient and/or said composition improves the state of skin by reducing the crow's feet and/or to hydrate the skin.

11. The method according to claim 8, wherein said effective amount of said active ingredient improves the state of skin by increasing the synthesis of hyaluronic acid in the cells of the skin.

12. The method according to claim 8, wherein said effective amount of said active ingredient improves the state of skin by increasing the synthesis of the hyaluronan synthase-2 in the cells of the skin.

13. A cosmetic composition for topical application, comprising an active ingredient according claim 1 in an amount between 0.1 and 3% by total weight of the composition.

14. A cosmetic process for inhibiting and/or to combating the effects of age on skin, comprising:
topically applying a composition according to claim 13.

15. A cosmetic process for inhibiting and/or to combating the effects of age on skin, comprising:
topically applying a composition containing an active ingredient obtained from *Metschnikowia agaves*, the active ingredient being a *Metschnikowia agaves* hydrolyzate.

16. The active ingredient according to claim 1, comprising α-glucan oligosaccharides and β-glucan oligosaccharides.

17. The active ingredient according to claim 1, wherein said *Metschnikowia agaves* hydrolyzate is obtained by enzymatic hydrolysis of *Metschnikowia agaves* with α-amylase and β-glucanase.

* * * * *